United States Patent [19]
Yamamoto et al.

[11] Patent Number: 6,008,364
[45] Date of Patent: Dec. 28, 1999

[54] PROCESS FOR PRODUCING ALKENYL–SUBSTITUTED PYRIDINE DERIVATIVE

[75] Inventors: Michio Yamamoto, Otsu; Gohfu Suzukamo, Suita, both of Japan

[73] Assignee: Sumitomo Chemical Company, Limited, Osaka, Japan

[21] Appl. No.: 09/112,981

[22] Filed: Jul. 10, 1998

[30] Foreign Application Priority Data

Jul. 14, 1997 [JP] Japan ................................. 9-188184
Aug. 7, 1997 [JP] Japan ................................. 9-212943

[51] Int. Cl.$^6$ ................................................. C07D 211/70
[52] U.S. Cl. ........................................... 546/352; 546/351
[58] Field of Search ...................................... 546/352, 351

[56] References Cited

U.S. PATENT DOCUMENTS 1,934,123  11/1933  Hofmann et al. ........................... 585/24

FOREIGN PATENT DOCUMENTS 557514  8/1932  Germany.

OTHER PUBLICATIONS

Arbuzov et al., Chemical Abstracts, vol. 39, No. 6, p. 1945, Mar. 20, 1945 (XP–002078278).

Wegler et al., Chem. Ber., vol. 83, No. 1, pp. 6–10 (1950) (XP–002078275).

Pines et al., J. Org. Chem., vol. 32, pp. 3183–3188 (1967) (XP–002078276).

Selimov et al., Russian Chemical Bulletin, vol. 42, No. 5, pp. 872–878 (May 1993) (XP–002078277).

Pines et al., *Base–Catalyzed Reactions*, XXXII, vol. 32, pp. 3183–3188 (Oct. 1967).

Miyata, *Clays and Clay Minerals*, vol. 23, pp. 369–375 (1975).

*Primary Examiner*—D. Margaret Mach
*Attorney, Agent, or Firm*—Birch, Stewart, Kolasch & Birch, LLP

[57] ABSTRACT

There is provided a process for producing an alkenyl-substituted pyridine derivative using, a solid base catalyst which is obtained by heating a metal oxide selected from the group consisting of alumina, an alkaline earth metal oxide and a hydrotalcite with

- an alkali metal,
- an alkali compound and an alkali metal or
- an alkali compound and an alkali metal hydride under an inert gas atmosphere at a temperature within the range of 100–700° C.

17 Claims, No Drawings

PROCESS FOR PRODUCING ALKENYL—SUBSTITUTED PYRIDINE DERIVATIVE

BACKGROUND OF THE INVENTION

1. Field of the Invention

The present invention relates to a process for producing an alkenyl-substituted pyridine derivative which is useful for an intermediate of fine chemicals such as agrochemicals, pharmaceuticals and cosmetics.

2. Description of Related Art

It has been disclosed that an alkenyl-substituted pyridine can be obtained by reacting γ-alkylpyridine having a hydrogen atom at α-position of its side chain with butadiene in the presence of sodium or potassium, however, the process has not been satisfactory in that the reaction is accompanied by problems of a by-production of a large amount of dialkenylated product, a complicated separation of the catalyst from the product, and a problem of an insufficient catalytic activity [Herman Pines and Janusz Oszczapowicz, J. Org. Chem., 32, 3183 (1967)].

Therefore, a further process for producing the desired alkenyl-substituted pyridine in good selectivity has been desired.

SUMMARY OF THE INVENTION

The present invention provides:
a process for producing an alkenyl-substituted pyridine, which comprises reacting:
  i) an alkylpyridine having a hydrogen atom on α-position of its side chain with
  ii) a conjugated diene in the presence of
  iii) a solid base which is obtained under an inert gas atmosphere at a temperature within the range of 100–700° C. by heating:
    iii-a) a metal oxide selected from the group consisting of alumina, an alkaline earth metal oxide and a hydrotalcite, with
    iii-b1) an alkali metal,
    iii-b2) an alkali compound and an alkali metal or
    iii-b3) an alkali compound and an alkali metal hydride.

According to the present process, the desired alkenyl-substituted pyridine is produced in good yield with a catalytic amount of the catalyst, which can be readily separated from the reaction product.

DESCRIPTION OF PREFERRED EMBODIMENT

A description will be made to the solid base catalyst which is obtained at a temperature of 100–700° C. under an atmosphere of an inert gas by heating:
  i') a metal oxide selected from the group consisting of alumina, an alkaline earth metal oxide and a hydrotalcite, with
  ii'-a) an alkali metal,
  ii'-b) an alkali compound and an alkali metal, or
  ii'-c) an alkali compound and an alkali metal hydride.

A metal oxide selected from the group consisting of alumina, an alkaline earth metal oxide and a hydrotalcite is used for producing the solid base catalyst of the present invention.

As the alumina, aluminas of various forms may be used. Among them, aluminas having a large surface area, such as γ-type, ρ-type and χ-type, are preferably used.

As the alkaline earth metal compound, oxides of alkaline earth metal, such as Mg, Ca and Ba, are preferably employed.

Hydrotalcites hereinafter include hydrotalcite-like compounds as disclosed in "The syntheses of hydrotalcite-like compounds and their structures and physico-chemical properties", Clays and Clay Minerals. Vol. 23. pp.369–375 Pergamon Press 1975. Printed Great Britain, the whole content of which is incorporated herein by reference. Hydrotalcites comprising various combinations of metals may be used. Hydrotalcite which is prepared from a magnesium compound and an aluminum compound is preferably used.

The solid base is prepared by heating under an inert gas atmosphere the metal oxide with:
  an alkali metal,
  an alkali compound and an alkali metal, or
  an alkali compound and an alkali metal hydride.

When the alkali metal is used, sodium or potassium is usually used alone or in combination. At least one element of group I of Periodic Table, such as lithium, sodium, potassium and rubidium, can be used, as the alkali metal. The amount of the alkali metal to be used is usually 2–20% by weight of the metal oxide. The heating temperature is usually 100–700° C., preferably 100 to 600° C.

When the alkali compound and alkali metal are used, the solid base is preferably prepared by heating the metal oxide with an alkali compound, and then allowing the resulting to react with the alkali metal or the alkali metal hydride.

As the alkali compound, oxides, hydroxides and alkoxides of elements belonging to group I or group II of Periodic Table may be employed. Oxides and hydroxides of sodium, potassium, rubidium, cesium, magnesium and calcium are preferably used. Two or more alkali compounds may be employed. The amount of the alkali compound is usually 5–50% by weight of the metal oxide.

The alkali compound is usually reacted with the metal oxide directly in a powder-form or a flake-form. It also may be dissolved or dispersed in a solvent, such as water and an organic solvent, then added to the metal oxide, and subsequently heated at a predetermined temperature. The heating temperature is usually from 100° C. to 700° C., preferably from 150° C. to 400° C.

As the alkali metal, the same alkali metal as described above can be used.

Examples of the alkali metal hydride include sodium hydride and potassium hydride. The amount of the alkali metal hydride to be used is normally 2–20%, preferably 4–18% by weight of the metal oxide.

The alkali metal or the alkali metal hydride is usually heated within the range of 100–700° C., preferably 120–500° C.

The heating time can be optionally set, for example, the time for reacting the alkali compound can be typically set 0.5–10 hours and that for reacting the alkali metal or the alkali metal hydride can be typically set 0.1–5 hours.

Examples of the inert gas include nitrogen, helium and argon.

Thus, a solid base, which is good in fluidity and easy to be handled and exhibits a good catalytic activity in the reaction, can be obtained.

The alkylpyridine used in the present invention includes both a monoheterocyclic compound and a fused heterocyclic compound.

More specifically, the alkylpyridine includes a pyridine:
  having at least one (C1–C4)alkyl group wherein two adjacent alkyl groups may form an alkylene or aromatic ring which may be substituted with a (C1–C3)alkyl group, and having at least one hydrogen atom at α-position of the alkyl group bonded to the pyridine ring.

Specific examples of the pyridine compound include: methylpyridine(e.g. 2-methylpyridine, 3-methylpyridine, 4-methylpyridine), ethylpyridine(e.g. 2-ethylpyridine, 3-ethylpyridine, 4-ethylpyridine), n-propylpyridine(e.g. 2-n-propylpyridine, 3-n-propylpyridine, 4-n-propylpyridine), isopropylpyridine(e.g. 2-i-propylpyridine, 3-i-propylpyridine, 4-i-propylpyridine), n-butylpyridine(e.g 2-n-butylpyridine, 3-n-butylpyridine, 4-n-butylpyridine), sec-butylpyridine(e.g. 2-sec-butylpyridine, 3-sec-butylpyridine, 4-sec-butylpyridine), isobutylpyridine(e.g. 2-i-butylpyridine, 3-i-butylpyridine, 4-i-butylpyridine), dimethylpyridine(e.g 2,4-dimethylpyridine, 2,6-dimethylpyridine, 2,3-dimethylpyridine), diethylpyridine (e.g. 2,4-diethylpyridine, 2,6-diethylpyridine, 2,3-diethylpyridine), di-n-propylpyridine (e.g. 2,4-di-n-propylpyridine, 2,6-di-n-propylpyridine), diisopropylpyridine(e.g. 2,4-di-i-propylpyridine, 2,6-di-i-propylpyridine), di-n-butylpyridine(e.g. 2,4-di-n-butylpyridine, 2,6-di-n-butylpyridine), di-sec-butylpyridine (e.g. 2,4-di-sec-butylpyridine, 2,6-di-sec-butylpyridine), diisobutylpyridine(e.g. 2,4-di-i-butylpyridine, 2,6-di-i-butylpyridine), trimethylpyridine(e.g. 2,4,6-trimethylpyridine), triethylpyridiene(e.g. 2,4,6-triethylpyridine), tripropylpyridine(e.g. 2,4,6-triisopropylpyridine), 2-methyltetrahydroquinoline, tetrahydroquinoline, methylquinoline and ethylguinoline. Among them, a pyridine compound having at least one (C1–C4)alkyl group is preferred. Pyridine compounds having at least one methyl group are more preferred. Particularly, methylpyridine is preferably used.

As the conjugated diene, linear or branched conjugated dienes having 4–10 carbon atoms are normally used. Examples thereof include 1, 3-butadiene, 2-methyl-1, 3-butadiene, 1, 3-pentadiene, 1, 3-hexadiene. Among them, 1, 3-butadiene and 2-methyl-1, 3-butadiene are preferably employed.

The alkenylation reaction can be conducted either by a batch method or a flow method using a fixed bed or a fluid bed.

The conjugated diene is reacted with the alkylpyridine in the presence of the solid base catalyst usually within the range of 20–200° C., preferably 50–170° C. The reaction pressure is generally within the range of from atmospheric pressure to 20 kg/cm$^2$ (gauge), preferably from atmospheric pressure to 3 kg/cm$^2$ (gauge). The molar ratio of the conjugated diene used to the alkylpyridine used normally ranges from 0.01:1 to 10:1, preferably from 0.05:1 to 0.6:1.

An amount of the catalyst used in the batch method is generally within the range of 0.05–30% by weight, preferably 0.1–10% by weight, based on the alkylpyridine used. The reaction time is generally within the range of 0.1–5 hours, preferably 0.3–2 hours.

The total supplying velocity of the alkylpyridine and the conjugated diene in the flow reaction normally ranges from 0.01 to 10 hr$^{-1}$, preferably from 0.1 to 3 hr$^{-1}$.

Using the solid base catalyst of the present invention, the alkenyl-substituted pyridine can be efficiently produced. Additionally, according to the present invention, a desired alkenyl-substituted pyridine can be produced very efficiently even using a small amount of the catalyst under a gentle condition. Furthermore, the process of the present invention is advantageous because it is very easy in posttreatment after reaction as well as in handling the catalyst.

EXAMPLE

The following Examples further illustrate the present invention in detail but are not to be construed to limit the scope thereof.

Preparation of Solid Base A 25 g of active alumina (manufactured by Sumitomo Chemical Co., Ltd.), which had a size of 100–200 meshes, was heated for 1 hour at 500° C. with stirring under an atmosphere of nitrogen gas, and then cooled to 350° C. After adding 5.88 g of potassium hydroxide (an analytical grade reagent manufacture by Nacalai Tesque, Inc.) to the active alumina, the mixture was heated for 3 hours with stirring. After cooling the mixture to 300° C., 2.05 g of metallic sodium (a reagent manufactured by Nacalai Tesque, Inc.) was added, and the mixture obtained was heated for 0.5 hours under stirring. The mixture was cooled to room temperature to obtain solid base A.

Preparation of Solid Base B

According to the same manner as that described in the preparation of solid base A except for using 25 g of magnesium oxide (manufactured by Konoshima Chemical Co., Ltd.) in place of alumina and using 4.41 g of potassium hydroxide (an analytic grade reagent manufactured by Nacalai Tesque, Inc.) and 1.5 g of metallic sodium (a reagent manufactured by Nacalai Tesque, Inc.), solid base B was prepared.

Preparation of Solid Base C

According to the same manner as that described in the preparation of solid base B except for using 25 g of calcium oxide (manufactured by Junsei Chemical Co., Ltd.) in place of magnesium oxide, solid base C was prepared.

Preparation of Solid Base D

According to the same manner as that described in the preparation of solid base B except for using 25 g of hydrotalcite (manufactured by Kyowa Kagaku K. K.) in place of magnesium oxide, solid base D was prepared.

Preparation of Solid Base E 25 g of active alumina (manufactured by Sumitomo Chemical Co., Ltd.), which had a size of 100–200 meshes, was heated for 1 hour at 500° C. with stirring under an atmosphere of nitrogen gas, and then cooled to 350° C. After adding 14.5 g of potassium hydroxide (an analytical grade reagent manufacture by Nacalai Tesque, Inc.) to the active alumina, the mixture was heated for 3 hours with stirring. After cooling the mixture to 300° C., 1.5 g of metallic potassium (a reagent manufactured by Nacalai Tesque, Inc.) was added, and the mixture obtained was heated for 0.5 hours with stirring. The mixture was cooled to room temperature to obtain solid base E.

Preparation of Solid Base F

According to the same manner as that described in the preparation of solid base E except for using 12.5 g of sodium hydroxide (an analytical grade reagent manufactured by Nacalai Tesque, Inc.) in place of 14.5 g of potassium hydroxide, solid base F was prepared.

Example 1

220 g of 4-methylpyridine and 1.0 g of solid base A were fed into a 1000 ml autoclave equipped with an electromagnetic stirrer under an atmosphere of nitrogen, and then heated to 140° C. with stirring at 700 r.p.m. subsequently, 16.5 g of butadiene was added to the mixture in 1 hour. After the reaction, the autoclave was cooled and the catalyst was removed by filtration. The reaction solution was analyzed by gas chromatography. 4-(3-pentenyl)pyridine was obtained in a 86% yield based on 4-methypyridine consumed.

Example 2

According to the same manner as that described in Example 1 except for using solid base B in place of solid base A, 4-(3-pentenyl)pyridine was obtained in a 84% yield based on 4-methypyridine consumed.

Example 3

According to the same manner as that described in Example 1 except for using solid base C in place of solid base A, 4-(3-pentenyl)pyridine was obtained in a 82% yield based on 4-methypyridine consumed.

Example 4

According to the same manner as that described in Example 1 except for using solid base D in place of solid base A, 4-(3-pentenyl)pyridine-was obtained in a 82% yield based on 4-methypyridine consumed.

Example 5

According to the same manner as that described in Example 1 except for using solid base E in place of solid base A, 4-(3-pentenyl)pyridine was obtained in a 84% yield based on 4-methypyridine consumed.

Example 6

According to the same manner as that described in Example 1 except for using solid base F in place of solid base A, 4-(3-pentenyl)pyridine was obtained in a 84% yield based on 4-methypyridine consumed.

Example 7

According to the same manner as that described in Example 1 except for using 2-methylpyridine in place of 4-methylpyridine, 2-(3-pentenyl)pyridine was obtained in a 86% yield based on 2-methypyridine consumed.

Example 8

According to the same manner as that described in Example 1 except for using 2, 4-lutidine in place of 4-methylpyridine, a 4:1 mixture of 2-(3-pentenyl)-4-methylpyridine and 2-methyl-4-(3-pentenyl)pyridine was obtained in a 85% yield based on 2, 4-lutidine consumed.

Preparation of Solid Base G 25 g of active alumina (manufactured by Sumitomo Chemical Co., Ltd.), which had a size of 100–200 meshes, was heated for 1 hour at 500° C. with stirring under an atmosphere of nitrogen gas, and then cooled to 300° C. After adding 2.5 g of potassium metal (an analytical grade reagent manufacture by Nacalai Tesque, Inc.) to the active alumina, the resulting was heated for 0.5 hour with stirring. After cooling the resulting to room temperature to obtain solid base G.

Preparation of Solid Base H

According to the same manner as that described in the preparation of solid base G except for using 25 g of magnesium oxide (manufactured by Konoshima Chemical Co., Ltd.) in place of alumina and 1.5 g of potassium metal (a reagent manufactured by Nacalai Tesque, Inc.), solid base H was prepared.

Preparation of Solid Base I

According to the same manner as that described in the preparation of solid base E except for using 25 g of calcium oxide (manufactured by Junsei Chemical Co., Ltd.) in place of magnesium oxide, solid base I was prepared.

Preparation of solid Base J

According to the same manner as that described in the preparation of solid bases except for using 25 g of hydrotalcite (manufactured by Kyowa Kagaku K. K.) in place of magnesium oxide, solid base J was prepared.

Example 9

220 g of 4-methylpyridine and 1.0 g of solid base G were fed into a 1000 ml autoclave equipped with an electromagnetic stirrer under an atmosphere of nitrogen, and then heated to 140° C. with stirring at 700 r.p.m. Subsequently, 16.5 g of butadiene was added to the mixture in 1 hour. After the reaction, the autoclave was cooled and the catalyst was removed by filtration. The reaction solution was analyzed by gas chromatography. 4-(3-pentenyl)pyridine was obtained in a 83% yield based on 4-methypyridine consumed.

Example 10

According to the same manner as that described in Example 9 except for using solid base H, 4-(3-pentenyl)pyridine was obtained in a 82% yield based on 4-methypyridine consumed

Example 11

According to the same manner as that described in Example 9 except for using solid base I, 4-(3-pentenyl)pyridine was obtained in a 82% yield based on 4-methypyridine consumed.

Example 12

According to the same manner as that described in Example 9 except for using solid base J, 4-(3-pentenyl)pyridine was obtained in a 82% yield based on 4-methypyridine consumed.

Example 13

According to the same manner as that described in Example 9 except for using 2-methylpyridine in place of 4-methylpyridine, 2-(3-pentenyl)pyridine was obtained in a 82% yield based on 2-methypyridine consumed.

Example 14

According to the same manner as that described in Example 9 except for using 2,4-lutidine in place of 4-methylpyridine, 2-(3-pentenyl)-4-methylpyridine and 2-methyl-4-(3-pentenyl)pyridine, the ratio between which was 2.5:1, was obtained in a 84% yield based on 2,4-lutidine consumed.

What is claimed is:

1. A process for producing an alkenyl-substituted pyridine drivative, which comprises reacting:
    i) an alkylpyridine having a hydrogen atom at α-position of its side chain with
    ii) a conjugated diene in the presence of
    iii) a solid base which is obtained under an inert gas atmosphere at a temperature within the range of 100–700° C. by heating:
        iii-a) a metal oxide selected from the group consisting of alumina, an alkaline earth metal oxide and a hydrotalcite, with
        iii-b1) an alkali metal,
        iii-b2) an alkali compound and an alkali metal or
        iii-b3) an alkali compound and an alkali metal hydride.

2. A process according to claim 1, wherein the solid base is obtained by heating a metal oxide as defined in claim 1 with an alkali metal.

3. A process according to claim 1, wherein the solid base is obtained by heating a metal oxide as defined in claim 1 with an alkali compound and an alkali metal or an alkali compound and an alkali metal hydride.

4. A process according to claim 1, wherein the solid base is obtained by heating a metal oxide as defined in claim 1 with an alkali compound and an alkali metal.

5. A process according to claim 1, wherein the solid base is obtained by heating a metal oxide as defined in claim 1 with an alkali compound and an alkali metal hydride.

6. A process according to claim 3, wherein the used amount of the alkali metal or alkali metal hydride is 2 to 20% by weight of the metal oxide.

7. A process according to claim 5, wherein the alkali metal or alkali metal hydride is heated at 120–500° C.

8. A process according to claim 1, wherein the reaction of the alkylpyridine with the conjugated diene is carried out at 20–200° C.

9. A process according to claim 8, wherein the reaction of the alkylpyridine with the conjugated diene is carried out at 50–170° C.

10. The process according to claim 1, wherein the solid base is obtained by heating in a temperature range of 100 to 600° C.

11. A process according to claim 1, wherein the alkylpyridine has at least one $C_1$–$C_4$ alkyl group, wherein two adjacent alkyl groups may form an alkylene or aromatic ring which may be substituted with $C_1$–$C_3$ alkyl group, and has at least one hydrogen atom at the alpha-position of the alkyl group bonded to the pyridine ring.

12. A process according to claim 1, wherein the conjugated diene is a linear or branched conjugated diene having 4–10 carbon atoms.

13. A process according to claim 11, wherein the conjugated diene is a linear or branched conjugated diene having 4–10 carbon atoms.

14. A process according to claim 1, wherein the conjugated diene is 1,3-butadiene or 2-methyl-1,-butadiene.

15. A process according to claim 1, wherein the alkylpyridine is methylpyridine.

16. A process according to claim 12, wherein the alkylpyridine is methylpyridine.

17. A process according to claim 14, wherein the alkylpyridine is methylpyridine.

* * * * *